(12) United States Patent
Sanders

(10) Patent No.: US 11,006,974 B2
(45) Date of Patent: May 18, 2021

(54) DEVICES FOR CREATING AN EPIDERMAL GRAFT SHEET

(71) Applicant: KCI LICENSING, INC., San Antonio, TX (US)

(72) Inventor: T. Blane Sanders, San Antonio, TX (US)

(73) Assignee: KCI LICENSING, INC., San Antonio, TX (US)

( * ) Notice: Subject to any disclaimer, the term of this patent is extended or adjusted under 35 U.S.C. 154(b) by 168 days.

(21) Appl. No.: 15/770,460

(22) PCT Filed: Nov. 3, 2016

(86) PCT No.: PCT/US2016/060336
§ 371 (c)(1),
(2) Date: Apr. 23, 2018

(87) PCT Pub. No.: WO2017/079439
PCT Pub. Date: May 11, 2017

(65) Prior Publication Data
US 2018/0368870 A1 Dec. 27, 2018

Related U.S. Application Data

(60) Provisional application No. 62/250,196, filed on Nov. 3, 2015.

(51) Int. Cl.
*A61B 17/322* (2006.01)
(52) U.S. Cl.
CPC .... *A61B 17/322* (2013.01); *A61B 2017/3225* (2013.01)

(58) Field of Classification Search
CPC .......... A61B 17/322; A61B 2017/3225; A61B 17/3217; A61B 17/3213; A61B 17/3211; A61B 17/32093; A61B 2017/32113; A61B 2017/32096; A61B 2017/320082;
(Continued)

(56) References Cited

U.S. PATENT DOCUMENTS

| 2,379,574 A | 7/1945 | Goldthwait |
| 2,579,029 A | 12/1951 | Barker et al. |
| 2,579,039 A | 12/1951 | Evans |

(Continued)

FOREIGN PATENT DOCUMENTS

| CN | 2125374 U | 12/1992 |
| CN | 2596950 Y | 1/2004 |

(Continued)

OTHER PUBLICATIONS

Ashley L. Howarth et al: "A novel approach to graft loss in burn using the CelluTome(TM) epidermal harvesting system for spot grafting: A case report", BURNS., vol. 41, No. 6, Sep. 1, 2015 (Sep. 1, 2015), pp. e57-e60.

(Continued)

*Primary Examiner* — Jocelin C Tanner
(74) *Attorney, Agent, or Firm* — Foley & Lardner LLP

(57) ABSTRACT

The present application relates to devices and methods for harvesting skin graft sheets. The present invention provides a blister raising device comprising a blade assembly for cutting a blister sheet and an array of protrusions configured to prevent a portion of skin at the donor site from blistering.

21 Claims, 10 Drawing Sheets

(58) Field of Classification Search
CPC .............. A61H 7/005; A61H 7/002; A61H 2201/1692; A61H 2201/169
See application file for complete search history.

(56) References Cited

U.S. PATENT DOCUMENTS

| | | | |
|---|---|---|---|
| 2,721,555 | A | 10/1955 | Jenny |
| 3,054,404 | A | 9/1962 | Meek |
| 3,782,387 | A | 1/1974 | Falabella |
| 4,345,374 | A | 8/1982 | Jacobson |
| 4,600,533 | A | 7/1986 | Chu |
| 4,605,010 | A | 8/1986 | McEwen et al. |
| 4,666,447 | A | 5/1987 | Smith |
| 4,679,324 | A | 7/1987 | Krik |
| 4,773,418 | A | 9/1988 | Hettich |
| 4,917,086 | A | 4/1990 | Feltovich et al. |
| 5,015,584 | A | 5/1991 | Brysk |
| 5,163,955 | A | 11/1992 | Love et al. |
| 5,386,633 | A | 2/1995 | Kanno |
| 5,433,221 | A | 7/1995 | Adair |
| 5,441,490 | A | 8/1995 | Svedman |
| 5,460,939 | A | 10/1995 | Hansbrough |
| 5,476,478 | A | 12/1995 | Jackson |
| 5,489,304 | A | 2/1996 | Orgill |
| 5,496,339 | A | 3/1996 | Koepnick |
| 5,545,222 | A | 8/1996 | Bonutti |
| 5,571,098 | A | 11/1996 | Domankevitz |
| 5,595,570 | A | 1/1997 | Smith |
| 5,624,451 | A | 4/1997 | Segal |
| 5,686,303 | A | 11/1997 | Korman |
| 5,730,717 | A | 3/1998 | Gelbfish |
| 5,759,193 | A | 6/1998 | Burbank |
| 5,792,173 | A | 8/1998 | Breen et al. |
| 5,817,115 | A | 10/1998 | Nigam |
| 5,888,219 | A | 3/1999 | Bonutti |
| 5,914,261 | A | 6/1999 | Korman |
| 5,914,264 | A | 6/1999 | Korman |
| 5,921,980 | A | 7/1999 | Kiru |
| 5,972,476 | A | 10/1999 | Field |
| 5,976,163 | A | 11/1999 | Nigam |
| 6,056,738 | A | 5/2000 | Marchitto |
| 6,063,094 | A | 5/2000 | Rosenberg |
| 6,071,247 | A | 6/2000 | Kennedy |
| 6,071,267 | A | 6/2000 | Zamierowski et al. |
| 6,080,166 | A | 6/2000 | McEwen et al. |
| 6,083,236 | A | 7/2000 | Feingold |
| 6,248,114 | B1 | 6/2001 | Ysebaert |
| 6,254,580 | B1 | 7/2001 | Svedman |
| 6,358,260 | B1 | 3/2002 | Ross |
| 6,364,908 | B1 | 4/2002 | Ysebaert |
| 6,402,770 | B1 | 6/2002 | Jessen |
| 6,436,078 | B1 | 8/2002 | Svedman et al. |
| 6,585,939 | B1 | 7/2003 | Dapprich |
| 6,612,310 | B2 | 9/2003 | Sklar |
| 6,623,498 | B1 | 9/2003 | Ziemer |
| 6,693,077 | B1 | 2/2004 | Ruben et al. |
| 6,800,282 | B1 | 10/2004 | Thomson |
| 6,860,904 | B2 | 3/2005 | Bonutti |
| 7,056,327 | B2 | 6/2006 | Levesque et al. |
| 7,078,582 | B2 | 7/2006 | Stebbings |
| 7,137,979 | B2 | 11/2006 | Conrad et al. |
| 7,207,998 | B2 | 4/2007 | Feingold |
| 7,208,006 | B2 | 4/2007 | Fleischman |
| 7,244,444 | B2 | 7/2007 | Bates |
| 7,513,902 | B2 | 4/2009 | Banbury et al. |
| 7,540,875 | B2 | 6/2009 | Jessen |
| 7,625,384 | B2 | 12/2009 | Eriksson |
| 7,651,507 | B2 | 1/2010 | Mishra |
| 7,666,134 | B2 | 2/2010 | Eriksson |
| 7,666,192 | B2 | 2/2010 | Seegert |
| 7,708,746 | B2 | 5/2010 | Eriksson |
| 7,727,700 | B2 | 6/2010 | Guu et al. |
| 7,926,401 | B2 | 4/2011 | Mishra |
| 8,002,779 | B2 | 8/2011 | Barker et al. |
| 8,109,187 | B2 | 2/2012 | Mishra |
| 8,162,957 | B2 | 4/2012 | Mishra |
| 8,187,285 | B2 | 5/2012 | Eriksson |
| 8,562,626 | B2 | 10/2013 | Sabir |
| 8,617,181 | B2 | 12/2013 | Sabir |
| 8,926,631 | B2 | 1/2015 | Sabir |
| 8,978,234 | B2 | 3/2015 | Sabir et al. |
| D729,386 | S | 5/2015 | Ziegler et al. |
| 9,173,674 | B2 | 11/2015 | Sabir et al. |
| 9,414,856 | B2 | 8/2016 | Sabir et al. |
| 9,451,979 | B2 | 9/2016 | Asrani |
| 9,517,082 | B2 | 12/2016 | Sabir et al. |
| 9,597,111 | B2 | 3/2017 | Sabir et al. |
| 9,610,093 | B2 | 4/2017 | Sabir et al. |
| 9,814,485 | B2 | 11/2017 | Pratt et al. |
| 9,848,908 | B2 | 12/2017 | Sabir et al. |
| 2001/0029380 | A1 | 10/2001 | Ysebaert |
| 2002/0052614 | A1 | 5/2002 | GeBauer |
| 2002/0092529 | A1 | 12/2002 | Rozier |
| 2003/0009185 | A1 | 1/2003 | Jessen |
| 2003/0069571 | A1 | 4/2003 | Treat et al. |
| 2003/0152909 | A1 | 8/2003 | Miranti |
| 2003/0212357 | A1 | 11/2003 | Pace |
| 2004/0097967 | A1 | 5/2004 | Ignon |
| 2004/0172045 | A1 | 9/2004 | Eriksson |
| 2004/0186498 | A1 | 9/2004 | Barnes et al. |
| 2004/0215217 | A1 | 10/2004 | Banbury |
| 2004/0225309 | A1 | 11/2004 | Eriksson |
| 2004/0230215 | A1 | 11/2004 | Eriksson |
| 2004/0237744 | A1 | 12/2004 | Lin |
| 2005/0038520 | A1 | 2/2005 | Binette |
| 2005/0076921 | A1 | 4/2005 | Rozier |
| 2005/0101972 | A1 | 5/2005 | Bhatavadekar |
| 2005/0221276 | A1 | 10/2005 | Rozakis et al. |
| 2005/0234485 | A1 | 10/2005 | Seegert |
| 2005/0244967 | A1 | 11/2005 | Pearlman |
| 2006/0079852 | A1 | 4/2006 | Bubb et al. |
| 2006/0141616 | A1 | 6/2006 | Guu |
| 2006/0173087 | A1 | 8/2006 | Hyde et al. |
| 2006/0206126 | A1 | 9/2006 | Sugimura |
| 2006/0247617 | A1 | 11/2006 | Danek et al. |
| 2006/0258956 | A1 | 11/2006 | Haberstich et al. |
| 2006/0271070 | A1 | 11/2006 | Eriksson |
| 2006/0287696 | A1 | 12/2006 | Wright et al. |
| 2007/0183974 | A1 | 8/2007 | Pearlman |
| 2007/0255168 | A1 | 11/2007 | Hiber et al. |
| 2008/0146980 | A1 | 6/2008 | Rousso |
| 2009/0085286 | A1 | 4/2009 | Grist et al. |
| 2009/0099122 | A1 | 4/2009 | Klinman et al. |
| 2010/0012311 | A1 | 1/2010 | Colongo |
| 2010/0042127 | A1 | 2/2010 | Eriksson |
| 2010/0121311 | A1 | 5/2010 | Seegert et al. |
| 2010/0145360 | A1 | 6/2010 | Eriksson |
| 2010/0152651 | A1 | 6/2010 | Boyden et al. |
| 2010/0152750 | A1 | 6/2010 | Memar |
| 2010/0286635 | A1 | 11/2010 | Watson, Jr. |
| 2010/0310823 | A1 | 12/2010 | Albertelli et al. |
| 2011/0009882 | A1 | 1/2011 | Remsburg et al. |
| 2011/0077664 | A1 | 3/2011 | Schulz |
| 2011/0230849 | A1 | 9/2011 | Coulthard et al. |
| 2011/0251602 | A1 | 10/2011 | Anderson |
| 2011/0264115 | A1 | 10/2011 | Asrani |
| 2011/0282309 | A1 | 11/2011 | Campbell et al. |
| 2012/0021186 | A1 | 1/2012 | Schneider |
| 2012/0035599 | A1 | 2/2012 | Sabir |
| 2012/0035618 | A1 | 2/2012 | Sabir |
| 2012/0035619 | A1 | 2/2012 | Sabir |
| 2012/0035620 | A1 | 2/2012 | Sabir |
| 2012/0041430 | A1 | 2/2012 | Anderson |
| 2012/0125798 | A1 | 5/2012 | Baecker et al. |
| 2012/0136323 | A1 | 5/2012 | Stasko et al. |
| 2012/0172894 | A1 | 7/2012 | Sabir et al. |
| 2012/0197267 | A1 | 8/2012 | Sabir |
| 2012/0201755 | A1 | 8/2012 | Rozakis et al. |
| 2012/0201793 | A1 | 8/2012 | Bellomo |
| 2012/0209226 | A1 | 8/2012 | Simmons et al. |
| 2012/0244623 | A1 | 9/2012 | Patel |
| 2012/0271320 | A1 | 10/2012 | Hall |
| 2013/0041385 | A1 | 2/2013 | Giovannoli |
| 2013/0145596 | A1 | 6/2013 | Sabir et al. |

(56) References Cited

U.S. PATENT DOCUMENTS

| | | |
|---|---|---|
| 2013/0158627 A1 | 6/2013 | Gozani |
| 2013/0165837 A1 | 6/2013 | Addison et al. |
| 2013/0204273 A1 | 8/2013 | Sabir et al. |
| 2014/0046344 A1 | 2/2014 | Sabir et al. |
| 2014/0074120 A1 | 3/2014 | Esarey |
| 2014/0277454 A1* | 9/2014 | Locke .................. A61F 2/0095 623/15.12 |
| 2014/0309662 A1* | 10/2014 | Brewer ................. A46B 9/028 606/131 |
| 2015/0127077 A1 | 5/2015 | Hanan |
| 2015/0182241 A1 | 7/2015 | Pratt |
| 2015/0182242 A1 | 7/2015 | Pratt et al. |
| 2015/0196224 A1 | 7/2015 | Rusu et al. |
| 2015/0201954 A1 | 7/2015 | Pratt et al. |
| 2015/0201955 A1 | 7/2015 | Sabir et al. |
| 2015/0238212 A1 | 8/2015 | Sabir et al. |
| 2016/0296663 A1 | 10/2016 | Higley et al. |
| 2017/0056041 A1 | 3/2017 | Sabir et al. |
| 2017/0128096 A1 | 5/2017 | Asrani et al. |
| 2017/0172599 A1 | 6/2017 | Sabir et al. |
| 2017/0224369 A1 | 8/2017 | Sabir et al. |

FOREIGN PATENT DOCUMENTS

| | | |
|---|---|---|
| CN | 101053528 A | 10/2007 |
| EP | 0099748 A1 | 2/1984 |
| EP | 1092515 A1 | 4/2001 |
| EP | 1614404 A2 | 1/2006 |
| EP | 2837370 A1 | 2/2015 |
| JP | 2009-095476 A | 5/2009 |
| SU | 772544 A1 | 10/1980 |
| WO | 1992011879 | 7/1992 |
| WO | 1995028886 | 11/1995 |
| WO | 1996018432 | 6/1996 |
| WO | 1996033768 | 10/1996 |
| WO | 1997020509 | 6/1997 |
| WO | 1998016158 | 4/1998 |
| WO | 2003020333 | 3/2003 |
| WO | 2003039382 | 5/2003 |
| WO | 2003049626 | 6/2003 |
| WO | 2003049783 | 6/2003 |
| WO | 03068120 A1 | 8/2003 |
| WO | 2003063680 A2 | 8/2003 |
| WO | 03093418 A2 | 11/2003 |
| WO | 2004028584 A1 | 4/2004 |
| WO | 2004071313 | 8/2004 |
| WO | 2004075764 | 9/2004 |
| WO | 2004078032 | 9/2004 |
| WO | 2004105576 | 12/2004 |
| WO | 2005033273 | 4/2005 |
| WO | 2005046428 | 5/2005 |
| WO | 2007034438 A2 | 3/2007 |
| WO | 2007117488 | 10/2007 |
| WO | 2010014716 A1 | 2/2010 |
| WO | 2010036788 A2 | 4/2010 |
| WO | 2011038326 | 3/2011 |
| WO | 2011059441 | 5/2011 |
| WO | 2011075676 | 6/2011 |
| WO | 2012019094 | 2/2012 |
| WO | 2012019095 | 2/2012 |
| WO | 2012019096 | 2/2012 |
| WO | 2012019098 | 2/2012 |
| WO | 2012087376 A1 | 6/2012 |
| WO | 2012102812 | 8/2012 |
| WO | 2012145504 | 10/2012 |
| WO | 2013049052 A2 | 4/2013 |
| WO | 2013086400 A1 | 6/2013 |
| WO | 2014152346 A1 | 9/2014 |
| WO | 20140152319 A2 | 9/2014 |
| WO | 2015103041 A1 | 7/2015 |
| WO | 2015103043 A1 | 7/2015 |
| WO | 2015103045 A1 | 7/2015 |
| WO | 2016081386 A1 | 5/2016 |
| WO | 2016164890 A1 | 10/2016 |
| WO | 2017049215 A1 | 3/2017 |
| WO | 2017079439 A1 | 5/2017 |
| WO | 2017087163 A1 | 5/2017 |
| WO | 2017143229 A1 | 8/2017 |

OTHER PUBLICATIONS

Canadian Examination Report, CA2982203, dated Dec. 31, 2019, 3 pages.
European Extended Search Report, 19201750.7, dated Feb. 4, 2020, 7 pages.
European Search Report, 16197729.3, dated May 2, 2017, 8 pages.
European Summons dated Oct. 31, 2019 for 16718801.0, 4 pages.
Examination Report dated Oct. 10, 2018 from corresponding EP Application No. 16 718 801.0, 4 pages.
Hachach-Haram: "The use of epidermal grafting for the management of acute wounds in the outpatient setting", Journal of Plastic, Reconstructive & Aesthetic Surgery, Sep. 1, 2015 (Sep. 1, 2015), pp. 1317-1318.
International Search Report and Written Opinion dated Apr. 2, 2019 for PCT/US2019/015230, 10 pages.
International Search Report and Written Opinion dated Apr. 25, 2019 for PCT/US2019/015504, 12 pages.
International Search Report and Written Opinion dated Feb. 20, 2019 for No. PCT/US2018/062973, 14 pages.
International Search Report and Written Opinion dated Mar. 29, 2019 for PCT/US2018/065815, 13 pages.
International Search Report and Written Opinion dated Oct. 29, 2019 for PCT/US2019/045216, 14 pages.
International Search Report and Written Opinion dated Sep. 14, 2018 for PCT/US2018/041399, 11 pages.
Meuleneire, "Soft silicone dressings made easy", Wounds International, May 1, 2013 (May 1, 2013), 6 pages.
Negative Pressure Instrument Operating and Maintenance Information For Models NP-2, NP-4 and NP-V, Apr. 30, 2004, 13 Pages.
Office Action dated Jul. 3, 2018 issued in related Japanese Patent Application No. 2016-502366, 5 pages.
Office Action dated Oct. 12, 2018 issued in related Chinese Patent Application No. 2016104166749, 13 pages.
Ozay Ozkaya, et al: "The effect of nonpreserved human amniotic membrane on the survival of ischaemic skin flaps in rats", Journal of Plastic, Reconstructive and Aesthetic Surgery, vol. 65, No. 12, Dec. 1, 2012 (Dec. 1, 2012), pp. 1700-1705.
Search Report dated Nov. 27, 2018 from corresponding EP Application No. 18 17 4326.1, 8 pages.
[No Author Listed] BBC-GCSE Bitsize: Gore-Tex, Article: http://www.bbc.co.uk/schools/gcsebitesize/science/ocr_gateway_pre_2011/carbon_chem/6_designer_polymers3.shtml; retrieved Apr. 22, 2015.
Awad, Chinese Cupping: A Simple Method to Obtain Epithelial Grafts for the Management of Resistant Localized Vitiligo, American Society of Dermatologic Surgery, Inc., Dermatol Surg, (2008), 34(9):1186-1193.
Balaji et al., Isolation of a Novel Population of Multipotent Stem Cells From Epidermal Layer of Human Skin, Biology and Medicine, (2010), 2(2):57-67.
Examination Report dated Nov. 17, 2017; received in Australian Application No. 2014239891 3 pages.
Extended European Search Report dated Apr. 30, 2014 received in European Application No. 11815367.5, 7 pages.
European Examination Report dated Mar. 18, 2015 corresponding to European Application No. 11815368.3 (4 sheets.).
European Search Report dated Apr. 17, 2015 received in European Application No. 12855127.2, 3 pages.
Extended European Search Report dated Mar. 10, 2016 received in European Application No. 14769345.1, 7 pages.
Extended European Search Report dated Mar. 3, 2016 received in European Application No. 14771124.6, 7 pages.
International Search Report and Written Opinion dated Aug. 1, 2014 for International Application No. PCT/US2014/027237, 12 pages.
International Search Report and Written Opinion dated Dec. 16, 2011 for International Application No. PCT/US11/46737, 8 pages.

(56) References Cited

OTHER PUBLICATIONS

International Search Report and Written Opinion dated Dec. 16, 2011 for International Application No. PCT/US11/46738, 6 pages.
International Search Report and Written Opinion dated Dec. 23, 2011 for International Application No. PCT/US11/46739, 6 pages.
International Search Report and Written Opinion dated Dec. 6, 2011 for International Application No. PCT/US11/46741, 6 pages.
International Search Report and Written Opinion dated Feb. 15, 2013 for International Application No. PCT/US2012/068551, 9 pages.
International Search Report and Written Opinion dated Jun. 28, 2016 for PCT/US2016/026918, 10 pages.
International Search Report and Written Opinion dated Mar. 19, 2015 for PCT/US2014/072170, 12 pages.
International Search Report and Written Opinion dated Mar. 19, 2015 for PCT/US2014/072188, 12 pages.
International Search Report and Written Opinion dated Mar. 20, 2015 for PCT/US2014/072180, 10 pages.
International Search Report and Written Opinion dated Oct. 2, 2014 for International Application No. PCT/US2014/027205, 19 pages.
International Search Report and Written Opinion dated Feb. 10, 2017 for International Application No. PCT/US2016/060336, 14 pages.
Invitation to Pay Additional Fees and, Where Applicable, Protest Fees dated May 26, 2017 for International Application No. PCT/US2017/018431, 20 pages.
Kreis et al., Expansion techniques for skin grafts: comparison between mesh and Meek Island (sandwich-) grafts, Burns, (1994), 20(1):S39-S42.
Lari et al., Expansion technique for skins grafts (Meek technique) in the treatment of severely burned patients, Burns, (2001), 27:61-66.
Meek et al., Successful Microdermagrafting Using the Meek-Wall Microdermatome, Am J Surg, (1958), 96(4):557-558.
Mulekar et al., Treatment of Vitiligo on Difficult-to-Treat Sites Using Autologous Noncultured Cellular Grafting, Dermatol Surg., (2009), 25(1):66-71.
Office Action dated Dec. 18, 2014 for U.S. Appl. No. 13/120,799.
Office Action dated Feb. 17, 2015 with English Text of Office Action corresponding to Japanese Patent Application No. 2013-523359, 2 pages.
Sams et al.. Useful adjuncts to harvest split-thickness skin grafts. Dermatol Surg. Dec. 2004;30(12 Pt 2):1591-2.
Weyandt et al., Split-skin grafting from the scalp: the hidden advantage. Dermatol Surg. Dec. 2009;35(12):1873-9.
International Search Report dated Jul. 26, 2017 from corresponding PCT/US2017/018431, pp. 8.
International Written Opinion dated Jul. 26, 2017 from corresponding PCT/US2017/018431, pp. 17.
Extended European Search Report received in EP Application No. 17186324.4 dated Nov. 20, 2017; 7 pages.
Office Action dated Jan. 3, 2018 issued in related Chinese Patent Application No. 2016104166749, 6 pages.
Office Action dated Feb. 24, 2018 issued in related Chinese Patent Application No. 2014800755616, 16 pages.

* cited by examiner

DEVICES FOR CREATING AN EPIDERMAL GRAFT SHEET

REFERENCE TO RELATED APPLICATIONS

This application claims priority to and is a National Stage of International Application No. PCT/US16/60336, filed on Nov. 3, 2016, entitled "Device For Creating An Epidermal Graft Sheet," which claims the benefit of and priority to U.S. Provisional Patent Application No. 62/250,196, filed Nov. 3, 2015, entitled "Devices For Creating An Epidermal Graft Sheet," the entirety of disclosures of which are incorporated herein by reference.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. As with any surgical procedure, skin grafting includes certain risks. Complications may include graft failure, rejection of the skin graft, infections at donor or recipient sites, or autograft donor sites oozing fluid and blood as they heal. Some of these complications (e.g., graft failure and rejection of the skin graft) may be mitigated by using an autograft instead of an allograft or a xenograft.

Moreover, skin grafts are often difficult to obtain due to the tendency of the skin layer being cut to curl or fold over onto itself or the surgical instrument (e.g., dermatome), thereby compromising the integrity of the graft and making it unsuitable for use. This folding/curling tendency is particularly problematic the thinner the layer is that is being obtained, such as the epidermal layer.

There is an unmet need for improved skin grafting methods and devices.

SUMMARY

The present invention generally relates to methods and devices for obtaining skin grafts. The devices for obtaining a skin graft, the device can include an array (e.g., a skin depression array). In some instances the device can include at least one array (e.g., 1, 2, 3, 4 or more). The array can be sized and shaped for positioning within an opening of the device. The array can comprise a plurality of interconnected protrusions, wherein the protrusions are configured to depress or contact portions of skin at a donor site during blister formation and thereby shielding the depressed portions from blistering.

The array can include a support frame. The support frame can include a plurality of apertures. The support frame can connect at least a portion of the plurality of interconnected protrusions.

The protrusions of the array can have a generally circular cross-section. The protrusions of the array can have a generally non-circular (e.g., square, rectangular, polygonal, oval, etc.) cross-section. The array can include about 2 to about 500 protrusions. The array can include about 10 to about 200 protrusions. The array can include at least 2, 5, 10, 20, 50, 75, 100, 125, 150, 175, 200, 300, 400, or 500 protrusions. The protrusions can be substantially uniform in size, shape or a combination thereof.

The protrusions can be substantially uniform in size. In some embodiments, the protrusions can range in size from about 1 mm to about 12 mm in diameter. In some embodiments, the protrusions can range in size from about 1 mm to about 3 mm in diameter. In some embodiments, the protrusions are about 2 mm in diameter.

The array can also include one or more separators. The separators are configured to depress or contact one or more areas of skin at the donor site such that more than one blister is raised at the donor skin.

The raised skin blister can be about 50%, about 60%, about 70% about 80%, about 90%, or about 95% of skin at the donor site. The raised skin blister can be about 50% to about 95% of skin at the donor site.

The devices for obtaining a skin graft can also include a blade assembly. The blade assembly can be configured to cut a raised skin blister sheet while sparing the shielded skin portions. The blade assembly can comprise a handle, at least one sliding arm, and a blade. The blade assembly is configured to cut into the skin and sever a large portion of the donor site while leaving behind "islands" of skin that were depressed by or in contact with the protrusions. The graft is preferably removed as a single sheet with a plurality of holes.

The devices for obtaining a skin graft can also include a hollow body, the hollow body can have a distal end configured for placement at a donor site. The hollow body can be further configured to raise a blister sheet at the donor site. The hollow body can also have a harvester head component and a harvester base component adapted to be joined together to define an inner chamber therebetween. The hollow body can also include an opening, adapted to receive at least one array.

The devices for obtaining a skin graft can also include a coupling port. The coupling port can place the inner chamber of the hollow body in communication (e.g., fluid, air, etc.) with a source of negative pressure. The source of negative pressure can induce formation of at least one (e.g., 1, 2, 3, 4 or more) skin blister at the donor site.

The devices can also include a heating element within the inner chamber of the hollow body. The heating element can include a heat source. The heating element can also conduct heat. The heating element can be integrated with the array. The heating element can be separate from the array. The heating element can induce formation of at least one (e.g., 1, 2, 3, 4 or more) skin blister at the donor site.

The skin blisters can be a single, continuous skin blister. The skin blisters can also be at least one (e.g., 1, 2, 3, 4 or more) skin blister. The skin blister can also be a plurality of skin blisters.

The devices for obtaining a skin graft can also include a substrate for application to the skin blister (skin graft sheet) and to transport the blister (skin graft) after it is cut from the donor site. The substrate can include a polymeric layer and an adhesive.

The present invention also relates to methods of harvesting a skin graft. The methods can include placing a distal end of a hollow body at a donor skin site. The hollow body can be configured to raise a blister sheet at the site. The methods can also include disposing at least one skin depression array within the hollow body, each array including a plurality of protrusions. The protrusions can be configured to contact portions of skin at the donor site, thereby preventing those portions of skin from blistering. The array can be configured for placement within the device during blister formation. The methods can further include raising at least one blister at the donor site and cutting the at least one raised blister.

The step of raising at least one blister can include applying a negative pressure, an elevated temperature, or a combination thereof to regions of skin within the hollow body that are in contact with the protrusions.

The method can also include removing the at least one skin depression array before the raising step.

The cutting of the at least one raised blister can include actuating a blade assembly. The blade assembly comprises a handle, at least one sliding arm, and a blade. The cutting of the at least one raised blister can produce a single, continuous graft. The cutting of the at least one raised blister can produce a plurality of skin grafts.

The method can further include contacting the raised blister sheet with a substrate to remove and transport the excised sheet graft. The substrate can be tacky, adhesive, or a combination thereof. The substrate can include a polymeric layer and an adhesive.

The type of blisters obtained by the methods and devices described herein can be any type, shape and/or size. For example, in certain embodiments, the blister can be a fluid-filled blister (e.g. a suction blister). In other embodiments, the blister is not fluid-filled, i.e., raised skin having only air within the blister. In some embodiments, the device can be used to raise any type of blister (e.g., fluid-filled or not fluid-filled).

The devices and methods can be configured to produce an epidermal graft, i.e., a graft that consists of substantially epidermal skin and does not include any substantial portion of the dermal layer.

DETAILED DESCRIPTION

Figure 1:
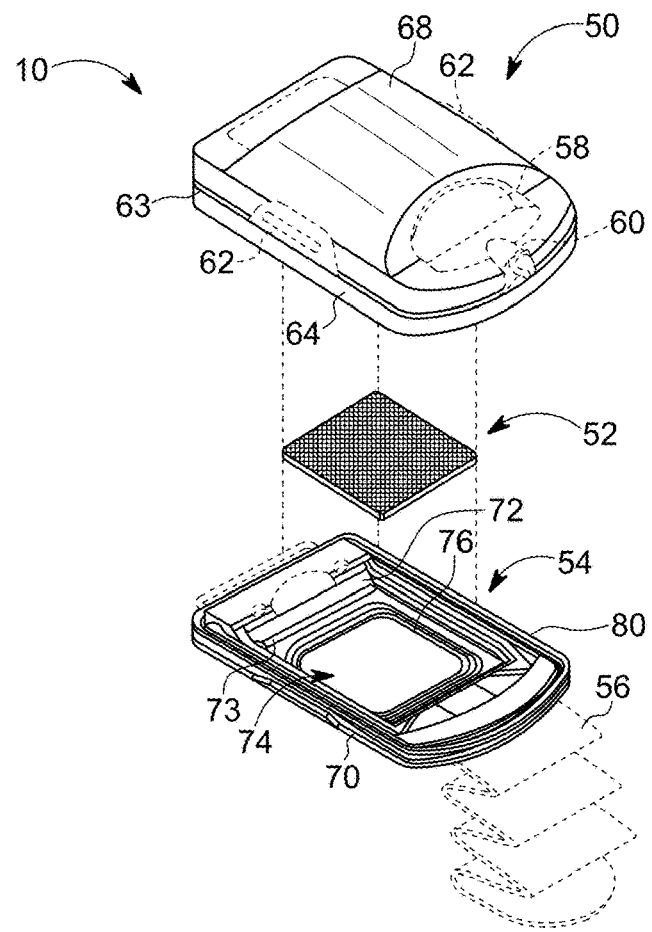
FIG. 1 is a schematic, exploded view of a skin graft harvesting apparatus according to the invention.

The present invention generally relates to devices and methods for obtaining a skin graft, e.g., an epidermal skin graft. The devices for obtaining a skin graft can comprise an array (e.g., a skin depression array). The devices can further comprise a blade assembly configured to cut a raised skin blister. The devices can further comprise a hollow body comprising a distal end configured for placement at a donor skin site and an opening defining a skin graft harvest area.

In some instances the device can include at least one array (e.g., 1, 2, 3, 4 or more). The array can be sized and shaped for positioning within an opening of the device. The array can comprise a plurality of interconnected protrusions, wherein the protrusions are configured to depress or contact portions of skin at a donor site during blister formation and thereby shielding the depressed portions from blistering. Each of the plurality of protrusions are interconnected forming an array such that a single, continuous raised skin blister can be pulled through or into the array.

In certain embodiments, devices of the invention are configured to produce epidermal skin grafts, leaving one or more areas of intact skin at a donor site. The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the two layers.

The dermis is a more complex structure. It is composed of two layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

In a skin graft, the characteristics of the donor site are more likely to be maintained after grafting to a recipient site as a function of the thickness of the dermal component of the graft. However, thicker grafts require more favorable conditions for survival due to the requirement for increased revascularization. It has been discovered, however, that a substantially epidermal graft according to the invention is more likely to adapt to the characteristics of the recipient site. Also, the skin grafts harvested include one or more holes. The one or more holes represent areas of skin left at the donor site to improve healing at the donor site and reduce the risk of secondary complications, e.g., infection.

An epidermal graft refers to a graft that consists of substantially epidermal skin and does not include any substantial portion of the dermal layer. A split thickness graft refers to a graft that includes sheets of superficial (epithelial) and some deep layers (dermal) of skin. A full-thickness graft refers to a graft that includes all of the layers of the skin including blood vessels.

Devices of the invention described herein may be used to harvest at least one skin graft (e.g., 1, 2, 3, 4 or more) for repair of numerous different types of skin damage. For example, harvested grafts may be used to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

In particular embodiments, the skin graft(s) are used to treat vitiligo. Vitiligo is a chronic disorder that causes depigmentation of patches of skin. It occurs when melanocytes, the cells responsible for skin pigmentation, die or are unable to function. Although patches are initially small, they often enlarge and change shape. When skin lesions occur, they are most prominent on the face, hands and wrists. Some lesions have hyper-pigmentation around the edges. Depigmentation is particularly noticeable around body orifices, such as the mouth, eyes, nostrils, genitalia and umbilicus.

Vitiligo is generally classified into two categories, non-segmental vitiligo and Segmental vitiligo. In non-segmental vitiligo (NSV), there is usually some form of symmetry in the location of the patches of depigmentation. New patches also appear over time and can be generalized over large portions of the body or localized to a particular area. Vitiligo where little pigmented skin remains is referred to as vitiligo universalis. Non-segmental vitiligo can come about at any age, unlike segmental vitiligo which is far more prevalent in teenage years.

Segmental vitiligo (SV) differs in appearance, aetiology and prevalence from associated illnesses. Its treatment is different from that of non-segmental vitiligo. It tends to affect areas of skin that are associated with dorsal roots from the spine. It spreads much more rapidly than non-segmental vitiligo and, without treatment, it is much more stable/static in course and not associated with auto-immune diseases.

To treat vitiligo, an autograft is provided to the site of depigmented skin. The graft includes melanocytes, and thus upon the recipient site accepting the graft, the graft will produce pigmented skin at the recipient site. A donor site of pigmented skin is aseptically cleaned prior to harvesting of a skin graft. Standard methods are used to clean the donor site. A typical donor site is an inner thigh, but any area of pigmented skin may be used.

After cleaning, a skin grafted is harvested using devices and methods of the invention. Devices described herein raise and cut a blister(s), such as a suction blister. The area of depigmented skin (i.e., the recipient site), is prepared through aseptic cleaning and dermabrasion. The graft(s) is applied to the dermabraded recipient site. The donor site and the recipient site are dressed and wound care is provided.

The present invention also relates to methods and devices for preparing and obtaining a skin graft from a donor site. In certain embodiments, methods of the invention allow for preparing a skin graft for transfer to a recipient site. The devices and methods of the invention use mechanical techniques for preparation of a skin graft. The devices for obtaining a skin graft can include a hollow body. The hollow body can have a distal end configured for placement at a donor skin site and can be configured to raise a blister sheet at the donor site. The devices can also include an array (e.g., a skin depression array) disposable in the hollow body and can include a plurality of interconnected protrusions. The protrusions are configured for placement within the device during blister formation to depress and/or contact portions of skin at the donor site during blister formation and thereby shield the depressed and/or contacted skin portions from blistering. The devices can also include a blade assembly configured to cut the raised skin blister sheet. The blade assembly does not cut the skin portions shielded and/or contacted by the protrusions.

In certain embodiments, a device is used to raise and cut a single punctuated skin graft sheet. The devices for obtaining a skin graft, the device can include a hollow body, the body can have a distal end configured for placement at a donor skin site and can be further configured to raise a blister sheet at the site, a skin depression array disposable in an opening of the hollow body and can include a plurality of protrusions, wherein the protrusions are configured to depress or contact portions of skin at the donor site during blister formation and thereby shield the depressed skin portions from blistering, and a blade assembly configured to cut the raised blister sheet while sparing the shielded skin portions.

The mechanism for raising a blister may be a vacuum component, a heating component, or a combination thereof. An exemplary heating component is a light source. In a particular embodiment, the mechanism is a combination of a vacuum component and a heating component.

FIG. 1 is a schematic, exploded perspective view of a skin graft harvester 10 according to the invention. In this illustrative embodiment, the harvester 10 includes a head component 50, a skin-contacting array of protrusions 52 and a harvester base component 54. The harvester base 54 is adapted for placement on a patient's skin at a donor site where skin grafts are to be obtained, e.g., on the inner thigh, and secured in place, for example, with strap 56 (shown in phantom).

Together the harvester head 50 and harvester base 54 can be adapted to be joined together to define an inner chamber therebetween and form a hollow body. The skin contacting array 52 can be configured to be disposed between the head and base within the hollow body such that protrusions (on the underside of array) are in contact with the donor skin site. As shown array 52 can be secured to the head 50, base 54, or both by a snap-fit rim 76. When the array is not deployed within the hollow body, the base 54 has an opening 74 to be placed over a target donor region of skin, from which a skin graft will be harvested. It should be clear that various other mechanisms can be used to secure the array 52 to either the head 50 or base 54 such that it can contact and engage the target donor skin region. For example, array 52 can be integrated with or simply be part of head 50. Array 52 and head 50 can then be secured to base 54 by securing means.

The harvester head 50 includes a detachable head portion 68 and a harvester body 64, which can contain a blade assembly 900 in accordance with the present teachings. The harvester body 64 can be adapted for placement on a patient's skin at a donor site where skin grafts are to be obtained (e.g., on the inner thigh), and can be secured in place so as to form a seal against the skin surface, for example, with a strap. The head portion 68 also includes a sealing surface or seal 63 such that when the head 50 and body 64 are joined together and the harvester head 50 is coupled to a vacuum pump via coupler 60, for example, a sealed compartment is defined for applying a reduced pressure to the patient's skin through one or more holes in the array assembly 52. The head portion 68 can also include means to house or secure array 52 within the head portion 68.

The head 50 can further include a seal 63 which permits a reduced pressure chamber to be formed when the head 50 and base 54 are joined together and the harvester 10 is coupled to a vacuum pump or other source of reduced pressure, e.g., via coupling port 60 connecting the harvester head 50 to its harvester base unit 54. The head 50 can optionally also include a heater (not shown) powered via the coupler 60 (or a separate conduit) adapted to couple with a power source in a base unit (not shown). The head 50 can further include one or more windows 58 for observation of skin blisters being formed within the chamber by application of reduced pressure, heat or both.

Once the blisters have been formed, the head 50 with or without array 52 can be removed, e.g., by deactivating the source of reduced pressure and by actuation of release levers 62, which break the seal 63 and allow the head 50 to be lifted off the harvester base 54. Head 50 and array 52 can be detached from harvester base 54 as a single component. Head 50 can also be lifted off base 54 first, and array 52, for example, can be detached from snap-fit rim 76 of the base 54 in a similar manner.

The harvester base 54 can include a sled 70, a cutting mechanism or blade assembly 72, and actuator handle 80. The cutting mechanism 72 can include a blade 73 for cleaving or cutting one or more skin grafts. In certain embodiments, the graft is preferably a single, continuous sheet formed by amalgamation of blisters throughout the target skin region except where the protrusions of array 51 have prevented blister formation by depressing and/or contacting portions of the skin. The skin graft sheet is typically "punctuated" or interrupted by holes where skin at the donor site has been spared. For example, FIGS. 3A-3I illustrate various examples of punctuated skin grafts obtained by the methods and devices described herein. As described in more detail below, these figures show examples of the skin grafts having one or more areas of skin that was not removed during cutting the skin blisters due to skin depression by the protrusions. In these examples, the holes in the skin graft sheet can comprise a pattern of holes. In the illustrated embodiment, the cutter mechanism is actuated by pulling up of handle 80 to cause the blade 72 to move horizontally across opening 74 and cleave the raised blister assemblage from the donor's skin. (An illustrative cutting mechanism is described in more detail below in connection with FIGS. 9A-9C.)

Figure 2:
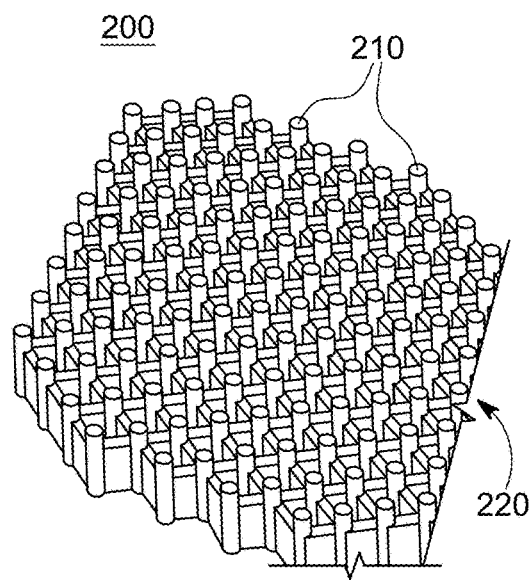
FIG. 2 illustrates an array of interconnected protrusions.

FIG. 2 shows an illustrative array 200 for use in the invention. Array 200 has a plurality of interconnected protrusions 210 connected by a support frame 220. The support frame 220 can include a plurality of apertures between each of the interconnected protrusions 210. The apertures or spacings between the protrusions can be configured so as to allow, for example, the conduction of heat and/or negative pressure between the protrusions. The spacing between the protrusions can also allow for exposed skin to blister. The support frame 220 can also allow the transfer of heat and/or negative pressure through the array 200. The support frame 220 can be a web that connects at least a portion of the plurality of protrusions. The support frame 220 and/or the plurality of interconnected columnar protrusions 210 can be frangible (e.g., broken or cut). The dimensions of the array 200 can be configured such that the raised blister is appropriately sized to be used as a skin graft. For example, the height of the connected array 200 can be configured such that the raised blister is appropriately sized to be used as an epidermal skin graft. The array can also be configured to sit inside the hollow body of the harvester device as described above in connection with FIG. 1.

The array 200 of protrusions 210 can be sized and shaped for positioning within an opening of the skin graft device. For instance, the array 200 can be a single component of the skin graft devices described herein. The array 200 can also be a removable component of the skin graft devices described herein. For example, one array can be swapped for another, different array (e.g., having a different size, cross-sectional shape, etc.). The array 200 can also be an integrated component of the skin graft devices described herein. In some embodiments, the array 200 can be sized so that at least 1 (e.g., 1, 2, 3, 4, 5, 6, or more) arrays can fit within the skin graft device. Therefore, the skin graft devices described herein can be configured to receive one or more arrays having different shapes, diameters, depths, spacing or combinations thereof, according to the type of skin graft needed.

As shown in FIG. 2, the array 200 can comprise a plurality of interconnected protrusions 210. The protrusions 210 are configured to depress or contact portions of skin at a donor site. The depression of skin or being in contact with skin prevents those areas to form blister.

In some embodiments, the protrusions 210 of array 200 can be substantially uniform in size, shape, or a combination thereof (e.g., symmetrically sized and/or shaped). In other embodiments, the protrusions of array are not substantially uniform in size, shape, or a combination thereof (e.g., asymmetrical). The protrusions 210 can be substantially uniform in size. In some embodiments, the protrusions can range in size from about 1 mm to about 12 mm in diameter. In some embodiments, the protrusions can range in size from about 1 mm to about 3 mm in diameter. In some embodiments, the protrusions are about 2 mm in diameter.

The array 200 can include about 2 to about 2000 protrusions. For example, the array 200 can include at least 2, 5, 10, 20, 50, 75, 100, 125, 150, 175, 200, 300, 400, or 500 protrusions. In some embodiments, there are about 2 to about 1000 protrusions in a single array. In another embodiment, there are about 10 to about 500 protrusions. In other embodiments, the number of protrusions is about 50 to 250 protrusions. In other embodiments, the number of protrusions is about 100 to about 200 protrusions.

FIG. 2 illustrates an array 200 where each of the one or more protrusions 210 have substantially the same cross-sectional shape. In some embodiments, the protrusions can comprise a pattern of protrusions 210. The protrusions 210 of the array 200 can have a generally circular cross-section. The protrusions 210 of the array 200 can have a generally non-circular (e.g., square, rectangular, polygonal, oval, etc.) cross-section. In other embodiments, each of the one or more protrusions can have a different cross-sectional shape. For example, an array can comprise protrusions having one or more (e.g., 2, 3, 4, 5 or more) shapes. For example, the protrusions can be combinations of substantially circular, semi-circular, rectangular, square, triangular, polygonal or other shapes.

The cross-sectional shape of the protrusion substantially determines the shape of skin left at the donor site, e.g., skin that does not blister and is not cut. FIGS. 3A-3I illustrate examples of skin grafts 300 obtained by using arrays having protrusions with different cross-sectional shapes. Each of the various shapes or holes 320 in the skin graft 300 is skin left at the donor site.

The size of the protrusions can range from about 1 mm to about 12 mm (e.g., in diameter, length, height, etc.). In some embodiments, each protrusion is less than 1 mm. In other embodiments, each protrusion is greater than 12 mm. In some embodiments, the protrusions are about 1 mm to about 3 mm. In another embodiment, the protrusions are about 2 mm.

The array of protrusions can also comprise any pattern. Exemplary patterns can result in the skin grafts 300 as shown in FIGS. 3A-3I. The size, shape, and pattern of the protrusions prevent the areas of skin in contact with the protrusions to blister. After the blister is cut, islands of intact areas of skin are left at the donor site, substantially the same shape, size (e.g., diameter) and pattern as the array of protrusions (see FIGS. 3A-3G). The array of protrusions can cause a single, contiguous blister to form and to be cut (e.g., by a blade assembly), which is easy to transport and graft at a recipient site.

The islands of skin left at a donor site, which correspond to holes 320 in FIGS. 3A-3I, can promote faster wound healing at the donor site and decrease the risk of infection. Also, the protrusions described herein allow for less skin to be removed at the donor site compared to a full sheet graft.

Figure 3A:
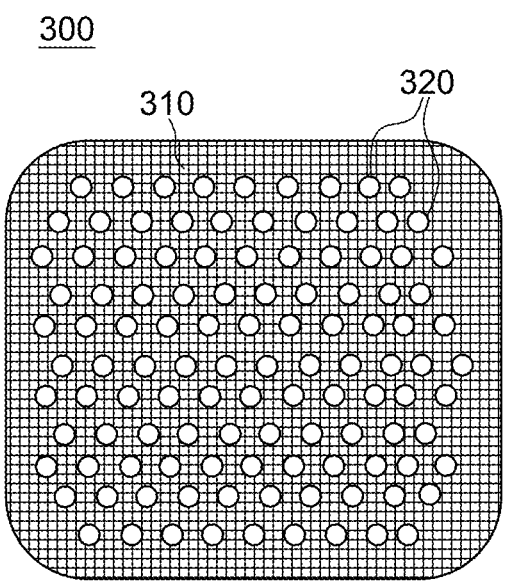
FIGS. 3A-3I illustrate examples of blister sheets obtained by the devices of the present invention.
Figure 3B:
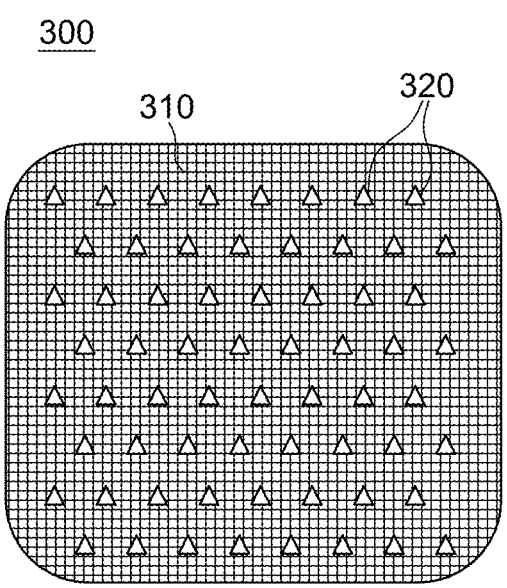
Figure 3C:
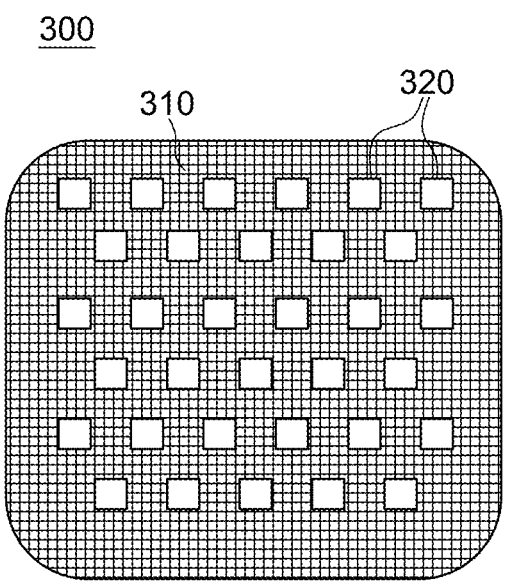
Figure 3D:
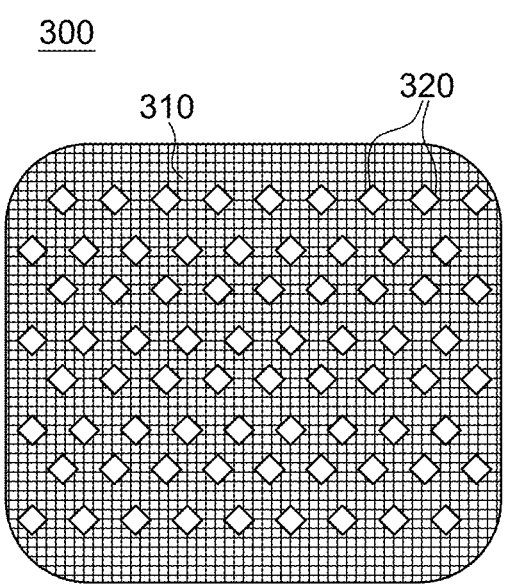
Figure 3E:
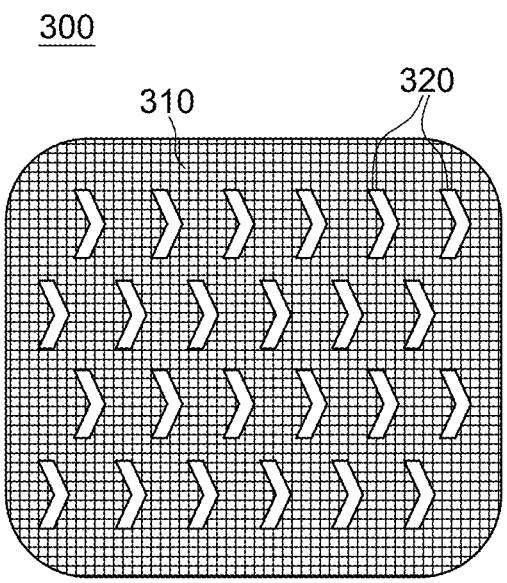
Figure 3F:
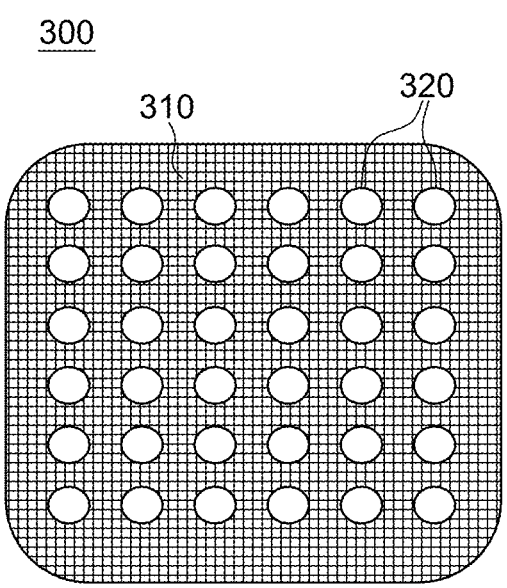
Figure 3G:
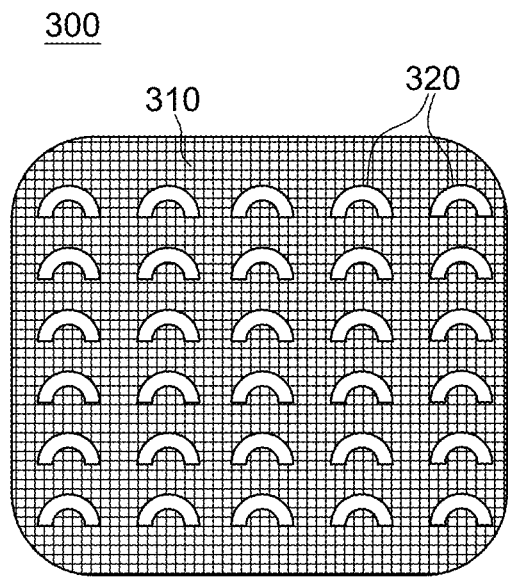
Figure 3H:
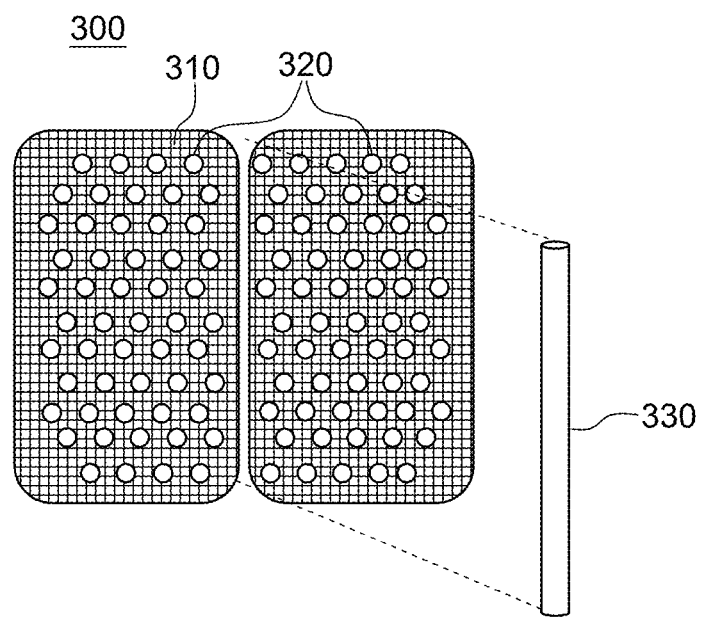
Figure 3I:
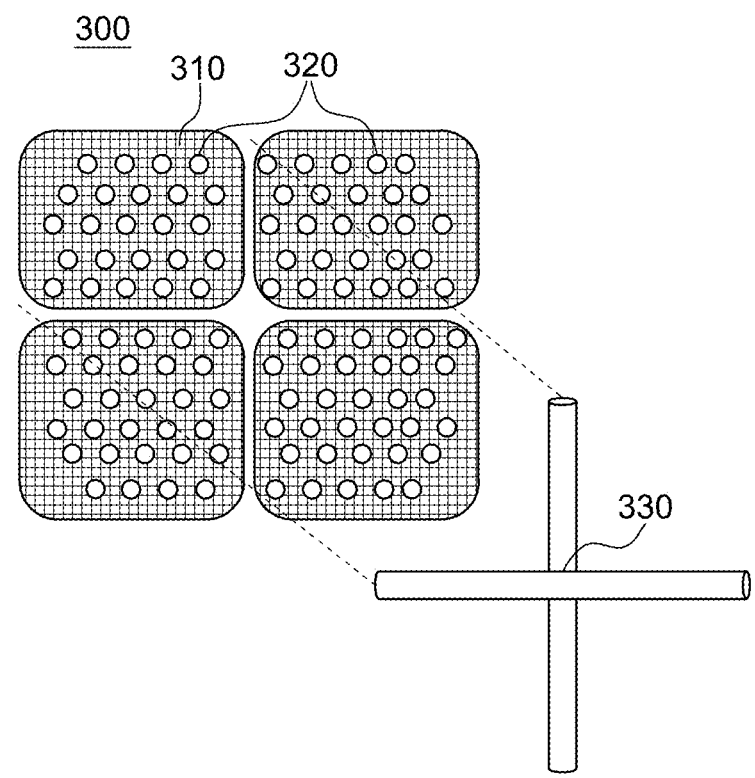

The array 200 can also include one or more separators 330 disposed within the array 200. The one or more separators 330 can be integrated with the array or can be separate. The separators 330 are configured (e.g., sized and/or shaped) to depress or contact one or more areas of skin at the donor site preventing (e.g., shielding) that skin to form a blister, thereby allowing more than one blister to be raised at the donor skin. Referring to FIG. 3H, separator 330 run substantially across array 200, thereby allowing for the formation of two separate skin blisters using the devices and methods described herein. Separator 330 depresses or contacts skin at the donor site to prevent the formation of a skin blister. In FIG. 3I, there are two separators 330 substantially in a "+" configuration. This configuration allows for the formation of four separate skin blisters using the devices and methods described herein. The separator 330 is configured to be sized and shaped so that enough skin between each skin blister is not cut when harvesting the grafts. The size (e.g., diameter, width) of the each of the one or more separators 330 is about 1 mm to about 10 mm. In some embodiments, the size of the separators is less than about 1 mm or more than about 10 mm. The length of the one or more separators is substantially the same as the length of the array 200. It will be readily apparently that any number of separators can be used to allow for the formation of any number of skin blisters.

The devices and methods described herein can produce a single, continuous sheet skin graft or a plurality of (e.g., 2, 3, 4, 5, 6 or more) skin grafts. A single graft can have areas of intact skin, sharing a common border, and other areas of no skin (e.g., caused by the array of protrusions). In some embodiments, more than one (e.g., 2, 3, 4, 5, 6 or more) skin graft can be obtained by the devices and methods described herein at a single donor site.

The raised skin blister and skin grafts generated (see FIGS. 3A-3I) can be about 50%, about 60%, about 70% about 80%, about 90%, or about 95% of the total skin at the donor site. For example, the raised skin blister can be about 50% to about 95% of skin at the donor site.

Figure 4:
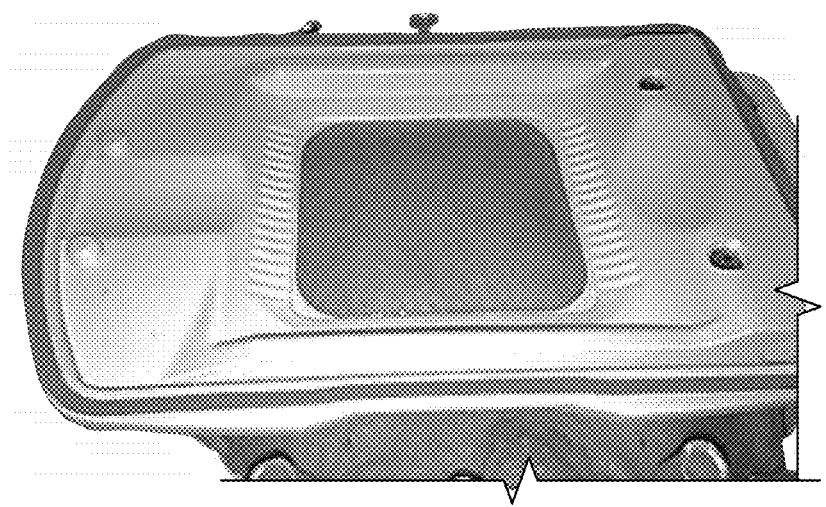
FIG. 4 is a photograph showing a harvester base according to the invention over a donor skin site.

FIG. 4 is a photograph showing an empty harvest base placed on top of a donor site. In some embodiments, the harvest area is about 5 cm by about 5 cm. In some embodiments, the harvest area is about 1 cm by about 1 cm, 2 cm by about 2 cm, 3 cm by about 3 cm or 4 cm by about 4 cm. In other embodiments the harvest area is greater than about 5 cm by about 5 cm. In some embodiments, the harvest area is about 1 cm to about 10 cm by about 1 cm to about 10 cm.

Figure 5:
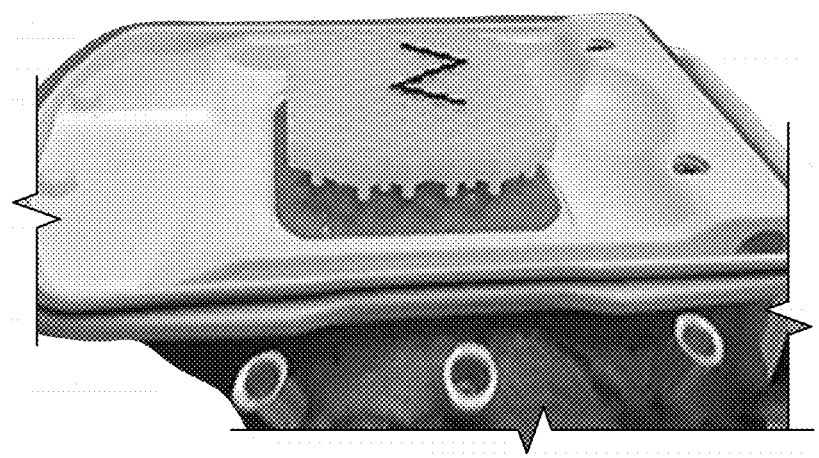
FIG. 5 is a photograph showing a skin-depressing protrusion array within a harvester base.

FIG. 5 is a photograph of an array of protrusions over an empty harvest member shown on the donor site.

Figure 6:
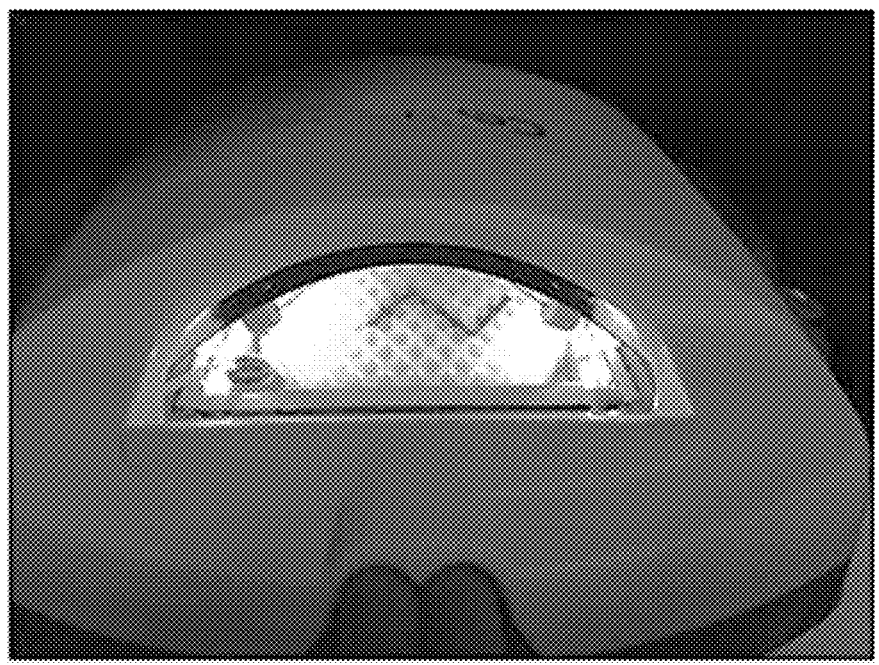
FIG. 6 is a photograph showing a device according to the invention with an array within a hollow body formed by the harvester head and base as used during a skin graft harvesting.

FIG. 6 illustrates an array of protrusions within a harvesting apparatus as used during harvest.

Figure 7:
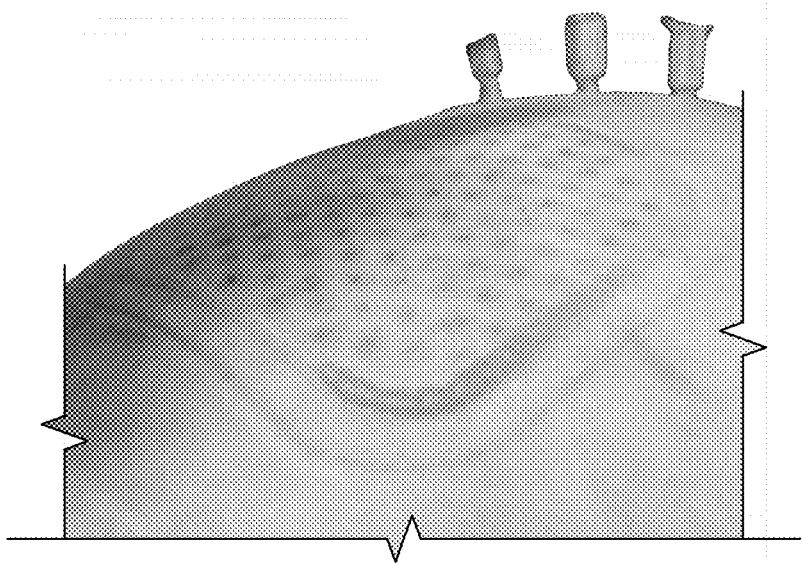
FIG. 7 is a comparative photograph illustrating a donor site following harvesting by a prior art method.
Figure 8:
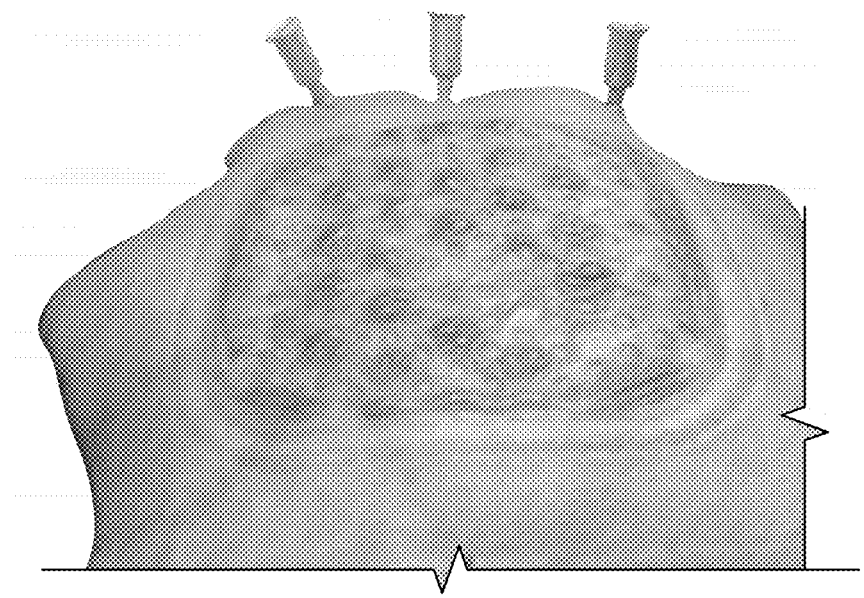
FIG. 8 is a photograph illustrating a donor site following harvesting according to the present invention with an array of protrusions.

FIGS. 7 and 8 are photographs of the donor sites after a skin graft was obtained with a CelluTome® device (FIG. 7) and with a device of the present invention (FIG. 8). FIG. 7 illustrates a plurality of microblisters can be cut and used as skin grafts, leaving large areas of intact skin behind at the donor site. FIG. 8 shows larger areas of blistered skin, with smaller areas of intact skin at the donor site.

Referring to FIGS. 4-8, blister formation is accomplished by attaching the distal end of a hollow body to donor site of a patient, such as an inner thigh of a patient (FIG. 4). Hook and loop fastener straps may be used to keep the device in place. An array of protrusions is positioned within the opening of the hollow body, as depicted in FIG. 5. A vacuum and/or heat source is connected to the device such that negative pressure can be generated within the device. For example, the device can include a heating element. To produce and harvest the skin graft, device is placed on a donor site, such as an inner thigh of a patient. The vacuum source is turned on, producing negative pressure within device (FIG. 6). The negative pressure causes skin not in contact with the protrusions 210 of the array 200 to blister. Such negative pressure results in the amalgamation of blisters into a blister sheet 300.

A heating component of blister raising mechanism provides a slight warming of array 200, which is in direct contact with the patient's skin surface. A heating component or conduit can be included or integrated as part of array 200. The application of a moderate negative pressure to the chamber interior from the vacuum component of blister raising mechanism, results in the patient's skin being gently drawn into the spaces (apertures) around the protrusions 210 in array 200. The result is a single blister, approximately the size of the opening in hollow body, i.e., harvest donor site 910 (See, e.g., FIGS. 3A-3I). The produced blister may be fluid-filled or may not contain any fluid, i.e., a blister having air within. The skin and blister area is generally not damaged and patient discomfort is minimal.

Once the blister is raised, the vacuum source and array can be removed. The raised blister can be cut (e.g., using a blade assembly) producing a single, continuous but punctuated skin graft (FIG. 8).

Figure 9A:
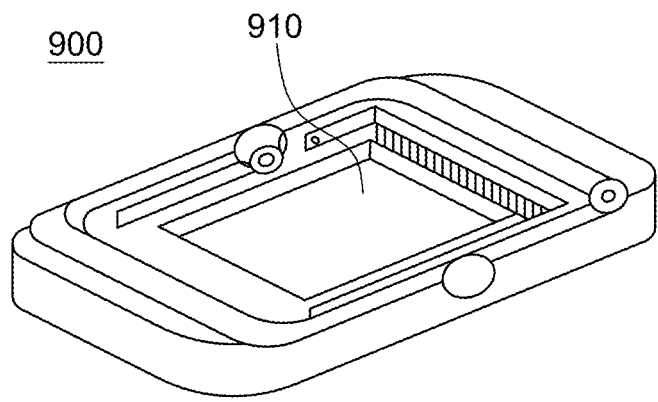
FIG. 9A-9C illustrate embodiments of a cutting mechanism for use in the present invention.
Figure 9B:
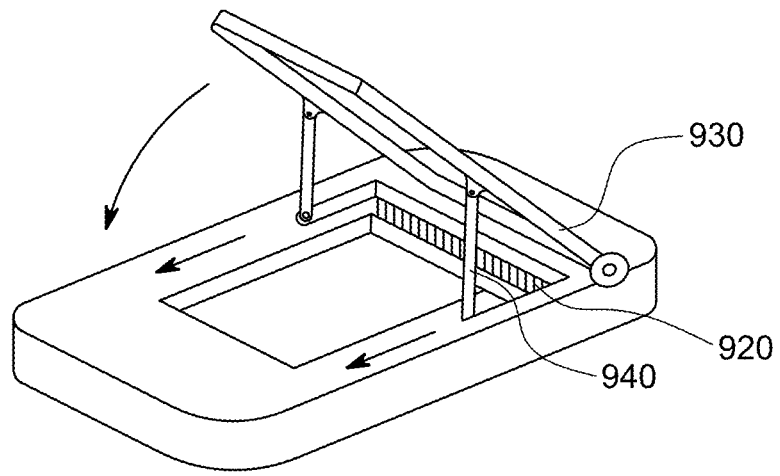
Figure 9C:
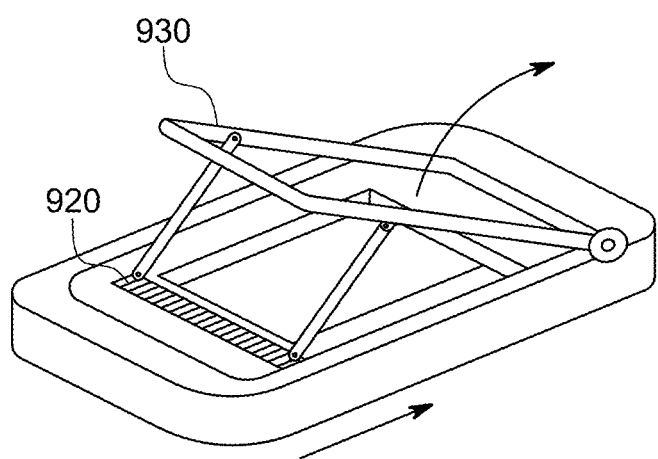

FIGS. 9A-9C further illustrate a cutting mechanism or blade assembly 900 for use in the present invention that does not interfere with the harvest area 910 until the time of harvesting a skin graft. The blade assembly 900 can be configured to cut a raised skin blister sheet while sparing the shielded skin portions. The blade assembly 900 can comprise a handle 930, at least one sliding arm 940, and a blade 920. The blade assembly 900 is configured to cut into the skin and sever a large portion of the donor site while leaving behind "islands" of skin that were depressed by or in contact with the protrusions 210 of array 200. The graft is preferably removed as a single, continuous sheet with a plurality of holes.

Components of blade assembly 900 lay flat and the blade 920 remains hidden, i.e., away from the harvest area. Blade 920 of blade assembly 900 can be retracted away from the harvest site 910 by pulling handle 930 up. As the handle 930 is pulled up, sliding arms 940 latch to the blade 920. After the sliding arms 940 latch blade 920, the blade 920 can then be deployed to advance from one side of the harvest site 910 to the other, opposite side. As the handle 930 is lowered, blade 920 slides through the harvest area 910, cutting a raised blister in the harvest site 910. Having the blade 920 hinged to the handle 930 allows a user to actuate the blade 920 from one side of the harvest area 910 to the other, opposite side of the with a single motion.

Additionally or alternatively, blade 920 can be pulled through the harvest area 910 as the handle 930 is lifted from a first position to a second position. In a first position, handle 930 lies flat against the blade assembly 900. In this position, sliding arms 940 are connected to blade 920. As the handle 930 is lifted, sliding arms drag blade 920 through the harvest area and cuts a raised blister in the harvest site 910.

The blade assembly 900 allows for a full epidermal sheet to be harvested with a single blade. Blade assembly 900 can be configured to accurately cut the raised blister at a predetermined depth. For example, a raised blister can be cut that is about 10 μm to about 1500 μm thick. In some embodiments, the harvest skin graft from the raised blister is about 10, 50, 100, 200, 500, 750, 1000, or 1500 μm thick.

The blade assembly 900 can be removable from base 54

As described herein, array 200 can be removable from base 54. In some embodiments, array 200 cannot be removed from base 54, e.g., array 200 is integrated with base 54. In these embodiments, the array 200 is not removed prior to cutting the raised blister with blade assembly 900. For example, blade 920 can be pulled through the harvest area 910, cutting a raised blister as well as portions of the protrusions 210 of array 200.

In some embodiments, the punctuated blister sheet can be captured on a substrate. For example, U.S. Publication 2014/0277454 discloses absorbent substrates for harvesting skin grafts, the contents of which are incorporated herein by reference. The devices for obtaining a skin graft can also include a substrate for application to the skin blister (skin graft sheet) and to transport the blister (skin graft) after it is cut from the donor site. The substrate can include a polymeric layer and an adhesive.

The amount of negative pressure applied, the amount of time the vacuum is maintained, and/or the size, shape, and/or length of the protrusions 210 in array 200 determine what type of graft will be harvested, e.g., epidermal graft, split thickness graft, or full thickness graft. Generally, the single, continuous graft will have an overall dimension of less than about 5 cm×about 5 cm. In some embodiments, the diameter or lateral dimension of the blister may be from about 1 cm to about 10 cm by about 1 cm to about 10 cm, although larger or smaller blister sizes can be used.

The present invention also relates to methods of harvesting a skin graft. The methods can include placing a distal end of a hollow body at a donor skin site. The hollow body can be configured to raise a blister sheet at the site. The methods can also include disposing at least one skin depression array within the hollow body, each array including a plurality of protrusions. The protrusions can be configured to contact portions of skin at the donor site, thereby preventing those portions of skin from blistering. The array can be configured for placement within the device during blister formation. The methods can further include raising at least one blister at the donor site and cutting the at least one raised blister.

The step of raising at least one blister can include applying a negative pressure, an elevated temperature, or a combination thereof to regions of skin within the hollow body that are in contact with the protrusions.

The method can also include removing the at least one skin depression array before the raising step.

The cutting of the at least one raised blister can include actuating a blade assembly. The blade assembly comprises a handle, at least one sliding arm, and a blade. The cutting of the at least one raised blister can produce a single, continuous graft. The cutting of the at least one raised blister can produce a plurality of skin grafts.

The method can further include contacting the raised blister sheet with a substrate to remove and transport the excised sheet graft. The substrate can be tacky, adhesive, or a combination thereof. The substrate can include a polymeric layer and an adhesive.

The type of blisters obtained by the methods and devices described herein can be any type, shape and/or size. For example, in certain embodiments, the blister can be a fluid-filled blister (e.g. a suction blister). In other embodiments, the blister is not fluid-filled, i.e., raised skin having only air within the blister. In some embodiments, the device can be used to raise any type of blister (e.g., fluid-filled or not fluid-filled).

The devices and methods can be configured to produce an epidermal graft, i.e., a graft that consists of substantially epidermal skin and does not include any substantial portion of the dermal layer.

The teachings of all patents, published applications and references cited herein are incorporated by reference in their entirety.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

What is claimed:

1. A device for obtaining a skin graft, the device comprising:
    a base having an opening;
    a skin depression array sized and shaped for positioning within the opening of the base and comprising a plurality of interconnected protrusions, wherein the protrusions are configured to depress portions of skin at a donor site during blister formation and thereby shield the depressed portions of skin from blistering; and
    a blade assembly coupled to the base and configured to cut a raised skin blister within the opening while sparing the shielded portions of skin.

2. The device of claim 1, wherein the blade assembly comprises a handle, at least one sliding arm, and a blade.

3. The device of claim 1, further comprising a hollow body, the hollow body having a distal end configured for placement at the donor site, wherein the hollow body is further configured to raise a skin blister at the donor site.

4. The device of claim 3, wherein the hollow body further comprises a harvester head component and a harvester base component adapted to be joined together to define an inner chamber therebetween.

5. The device of claim 4, further comprising a coupling port configured to place the inner chamber of the hollow body in communication with a source of negative pressure.

6. The device of claim 5, further comprising a heating element disposed within the inner chamber of the hollow body.

7. The device of claim 6, wherein the heating element comprises a heat source configured to conduct heat.

8. The device of claim 6, wherein the heating element is integrated with the skin depression array.

9. The device of claim 6, wherein the source of negative pressure and the heating element are configured to induce formation of at least one skin blister at the donor site.

10. The device of claim 9, wherein the at least one skin blister is a single, continuous skin blister.

11. The device of claim 1, wherein the skin depression array further comprises a support frame, wherein the support frame comprises a plurality of apertures and connects at least a portion of the plurality of interconnected protrusions.

12. The device of claim 1, wherein the protrusions have a generally circular cross-section.

13. The device of claim 12, wherein the array comprises one of about 2 to about 500 protrusions or about 10 to about 200 protrusions.

14. The device of claim 1, wherein the protrusions are substantially uniform in size.

15. The device of claim 1, wherein the array further comprises one or more separators, wherein each of the one or more separators are configured to depress one or more areas of skin at the donor site such that more than one blister is raised at the donor site.

16. The device of claim 1, wherein the raised skin blister is about 80% to about 95% of skin at the donor site.

17. A device for obtaining a skin graft, the device comprising:
- a hollow body configured to raise a blister sheet at the donor skin site, the hollow body comprising:
  - a distal end configured to be placed at a donor skin site; and
  - an opening defining a skin graft harvest area; and
- at least one array sized for removable positioning within the opening of the hollow body, the at least one array comprising a plurality of protrusions, wherein the protrusions are configured to contact portions of skin at a donor site and shield the contacted portions of skin from blistering; and
- a blade assembly configured to cut the raised blister sheet while sparing the portions of skin in contact with the protrusions.

18. The device of claim 17, wherein the array is removably replaceable with a different array.

19. The device of claim 18, wherein the different array comprises protrusions having at least one of a different shape, different diameter, different depth, or different spacing.

20. The device of claim 17, wherein protrusions are symmetrically sized and shaped.

21. The device of claim 17, wherein the protrusions are interconnected.

* * * * *

UNITED STATES PATENT AND TRADEMARK OFFICE
CERTIFICATE OF CORRECTION

PATENT NO. : 11,006,974 B2  Page 1 of 1
APPLICATION NO. : 15/770460
DATED : May 18, 2021
INVENTOR(S) : T. Blane Sanders It is certified that error appears in the above-identified patent and that said Letters Patent is hereby corrected as shown below:

In the Claims

Column 13
Line 21, In Claim 17, after "harvest area;", delete "and".

Signed and Sealed this
Ninth Day of April, 2024

Katherine Kelly Vidal
*Director of the United States Patent and Trademark Office*